(12) United States Patent
Li et al.

(10) Patent No.: US 9,795,595 B2
(45) Date of Patent: Oct. 24, 2017

(54) METHODS FOR TREATING CANCER

(71) Applicant: Boston Biomedical, Inc., Cambridge, MA (US)

(72) Inventors: Chiang Jia Li, Cambridge, MA (US); Youzhi Li, Westwood, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 15/114,465

(22) PCT Filed: Jan. 26, 2015

(86) PCT No.: PCT/US2015/012830
§ 371 (c)(1),
(2) Date: Jul. 27, 2016

(87) PCT Pub. No.: WO2015/112941
PCT Pub. Date: Jul. 30, 2015

(65) Prior Publication Data
US 2016/0339001 A1  Nov. 24, 2016

Related U.S. Application Data

(60) Provisional application No. 61/932,186, filed on Jan. 27, 2014, provisional application No. 61/938,391, filed on Feb. 11, 2014.

(51) Int. Cl.
*A61K 31/427* (2006.01)
*G01N 33/574* (2006.01)

(52) U.S. Cl.
CPC ......... *A61K 31/427* (2013.01); *G01N 33/574* (2013.01); *G01N 33/57496* (2013.01); *G01N 2333/82* (2013.01); *G01N 2333/912* (2013.01)

(58) Field of Classification Search
None
See application file for complete search history.

(56) References Cited

U.S. PATENT DOCUMENTS

2011/0124003 A1  5/2011  Ralph
2012/0252763 A1  10/2012  Li et al.

FOREIGN PATENT DOCUMENTS

WO   WO 2009/033033 A2 *  3/2009  ........... C07D 417/02

OTHER PUBLICATIONS

Meng, HM et al., Over expression of Nanog predicts tumor progression and poor prognosis in colorectal cancer, Cancer Biology and Therapy (2010) 9 (4), pp. 295-302.

* cited by examiner

*Primary Examiner* — Brian J Davis
(74) *Attorney, Agent, or Firm* — Finnegan, Henderson, Farabow, Garrett & Dunner LLP

(57) ABSTRACT

The invention provides thiazole-substituted indolin-2-ones as inhibitors of cancer stem cell pathway kinases (CSCPK) and related kinases, and methods of using these compounds, to treat subjects in need thereof.

28 Claims, No Drawings

METHODS FOR TREATING CANCER

FIELD OF THE INVENTION

The invention provides thiazole-substituted indolin-2-ones as inhibitors of cancer stem cell pathway kinases (CSCPK) and related kinases, and methods of using these compounds, to treat subjects in need thereof.

BACKGROUND OF THE INVENTION

Cancer fatalities in the United States alone number in the hundreds of thousands each year. Despite advances in the treatment of certain forms of cancer through surgery, radiotherapy, and chemotherapy, many types of cancer are essentially incurable. Even when an effective treatment is available for a particular cancer, the side effects of such treatment can be severe and result in a significant decrease in quality of life.

Most conventional chemotherapy agents have toxicity and limited efficacy, particularly for patients with advanced solid tumors. Chemotherapeutic agents cause damage to non-cancerous as well as cancerous cells. The therapeutic index of such compounds (a measure of the ability of the therapy to discriminate between cancerous and normal cells) can be quite low. Frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoesis, and nausea can occur. Depending on the general health of a patient, such side effects can preclude the administration of chemotherapy, or, at least, be extremely unpleasant and uncomfortable for the patient and severely decrease quality of the remaining life of cancer patients. Even for cancer patients who respond to chemotherapy with tumor regression, such tumor response often is not accompanied by prolongation of progression-free survival (PFS) or prolongation of overall survival (OS). As a matter of fact, cancer often quickly progress and form more metastasis after initial response to chemotherapy. Such recurrent cancers become highly resistant or refractory to chemotherapeutics. Such rapid recurrence and refractoriness, after chemotherapy, are considered to be caused by cancer stem cells.

Recent studies have uncovered the presence of cancer stem cells (CSC, also called tumor initiating cells or cancer stem-like cells) which have self-renewal capability and are considered to be fundamentally responsible for malignant growth, relapse and metastasis. Importantly, CSCs are inherently resistant to conventional therapies. Therefore, a targeted agent with activity against cancer stem cells holds a great promise for cancer patients (J Clin Oncol. 2008 Jun. 10; 26(17)). Therefore, while conventional chemotherapies can kill the bulk of cancer cells, they leave behind cancer stem cells. Cancer stem cells can grow faster after reduction of non-stem regular cancer cells by chemotherapy, which is considered to be the mechanism for quick relapse after chemotherapies.

STAT3 is an oncogene which is activated in response to cytokines and/or growth factors to promote proliferation, survival, and other biological processes. STAT3 is activated by phosphorylation of a critical tyrosine residue mediated by growth factor receptor tyrosine kinases, Janus kinases, or the Src family kinases. Upon tyrosine phosphorylation, STAT3 forms homo-dimers and translocates to the nucleus, binds to specific DNA-response elements in target gene promoters, and induces gene expression. STAT3 activates genes involved in tumorigenesis, invasion, and metastasis, including Bcl-xl, Akt, c-Myc, cyclin D1, VEGF, and survivin. STAT3 is aberrantly active in a wide variety of human cancers, including all the major carcinomas as well as some hematologic tumors. Persistently active STAT3 occurs in more than half of breast and lung cancers, colorectal cancers, ovarian cancers, hepatocellular carcinomas, and multiple myelomas, etc.; and more than 95% of head/neck cancers. STAT3 is considered to be one of the major mechanisms for drug resistance of cancer cells. However, STAT3 has proven a difficult target for discovering pharmaceutical inhibitor. So far, no direct inhibitor of STAT3 with clinically relevant potency has been identified after decades of efforts in the industry.

Accordingly, there exists a need for discovering compounds and pharmaceutical compositions for selectively targeting cancer cells, for targeting cancer stem cells, and for inhibiting STAT3, and methods of preparing these compounds, pharmaceutical compositions for clinical applications, and methods of administering the same to those in need thereof.

The references cited herein are not admitted to be prior art to the claimed invention.

SUMMARY

The invention provides compositions and methods using the following compound, referred to herein as the "Compound of the Invention":

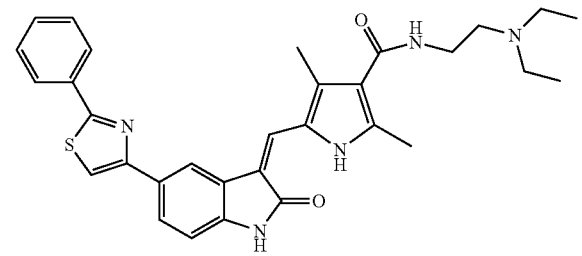 [SMILES: CCN(CC)CCNC(=O)c1c(C)[nH]c(/C=C2\C(=O)Nc3ccc(-c4csc(-c5ccccc5)n4)cc32)c1C]

This compound was described in the co-owned PCT application published as WO 2009/033033, the contents of which are incorporated herein in their entirety by reference. This compound is a selective inhibitor of cancer stem cell pathway kinases (CSCPK).

Cancer Stem Cells (CSC) are considered to be fundamentally responsible for malignant growth, relapse, metastasis, and resistance to conventional therapies. A variety of markers are used to identify CSCs, and one that shows high correlation to both stemness properties and drug resistance is NANOG. The compound of the disclosure is a cancer stemness kinase inhibitor with demonstrated ability to decrease stemness gene activities, including NANOG, in a broad panel of tumor cells and has shown potent anti-tumor and anti-metastatic activities preclinically. Furthermore, Phase I clinical trials show very promising signs of anti-cancer activity in patients.

A method according to the invention of treating, delaying the progression of, preventing a relapse of, alleviating a symptom of, or otherwise ameliorating a human, mammal, or animal subject afflicted with a neoplasm can include administering a therapeutically effective amount of the compound, product and/or pharmaceutical composition, so that anti-neoplastic activity occurs. For example, the anti-neoplastic activity can be anticancer activity. For example, the anti-neoplastic activity can include slowing the volume growth of the neoplasm, stopping the volume growth of the neoplasm, or decreasing the volume of the neoplasm. The neoplasm can include a solid tumor, a malignancy, a metastatic cell, a cancer stem cell. The neoplasm can include a carcinoma, a sarcoma, an adenocarcinoma, a lymphoma, or a hematological malignancy. The neoplasm can be refractory to treatment by chemotherapy, radiotherapy, and/or hormone therapy. The compound, product and/or pharmaceutical composition can be administered to prevent relapse of the neoplasm. The compound, product and/or pharmaceutical composition can be administered as an adjuvant therapy to surgical resection. The compound, product and/or pharmaceutical composition can be administered, for example, orally and/or intravenously.

Administration of the compounds, products and/or pharmaceutical compositions to a patient suffering from a disease or disorder is considered successful if any of a variety of laboratory or clinical results is achieved. For example, administration is considered successful one or more of the symptoms associated with the disease or disorder is alleviated, reduced, inhibited or does not progress to a further, i.e., worse, state. Administration is considered successful if the disorder, e.g., an autoimmune disorder, enters remission or does not progress to a further, i.e., worse, state.

In some embodiments, the compounds, products and/or pharmaceutical compositions described herein are administered in combination with any of a variety of known therapeutics, including for example, chemotherapeutic and other anti-neoplastic agents, anti-inflammatory compounds and/or immunosuppressive compounds. In some embodiments, the compounds, products and/or pharmaceutical compositions described herein are useful in conjunction with any of a variety of known treatments including, by way of non-limiting example, surgical treatments and methods, radiation therapy, chemotherapy and/or hormone or other endocrine-related treatment.

These "co-therapies" can be administered sequentially or concurrently. The compounds, products and/or pharmaceutical compositions described herein and the second therapy can be administered to a subject, preferably a human subject, in the same pharmaceutical composition. Alternatively, the compounds, products and/or pharmaceutical compositions described herein and the second therapy can be administered concurrently, separately or sequentially to a subject in separate pharmaceutical compositions. The compounds, products and/or pharmaceutical compositions described herein and the second therapy may be administered to a subject by the same or different routes of administration. In some embodiments, the co-therapies of the invention comprise an effective amount of the compounds, products and/or pharmaceutical compositions described herein and an effective amount of at least one other therapy (e.g., prophylactic or therapeutic agent) that has a different mechanism of action than the compounds, products and/or pharmaceutical compositions described herein. In some embodiments, the co-therapies of the present invention improve the prophylactic or therapeutic effect of the compounds, products and/or pharmaceutical compositions described herein and of the second therapy by functioning together to have an additive or synergistic effect. In certain embodiments, the co-therapies of the present invention reduce the side effects associated with the second therapy (e.g., prophylactic or therapeutic agents).

In some embodiments, the disease or disorder can be treated by administering the compound, product and/or pharmaceutical composition as follows. The blood molar concentration of the compound can be at least an effective concentration and less than a harmful concentration for a first continuous time period that is at least as long as an effective time period and shorter than a harmful time period. The blood molar concentration can be less than the effective concentration after the first continuous time period. For example, the effective concentration can be about 0.1 µM, about 0.2 µM, about 0.5 µM, about 1 µM, about 2 µM, about 3 µM, about 4 µM, about 5 µM, about 6 µM, about 10 µM, or another concentration determined to be effective by one of skill in the art. For example, the harmful concentration can be about 1 µM, about 3 µM, about 10 µM, about 15 µM, about 30 µM, about 100 µM, or another concentration determined to be harmful by one of skill in the art. For example, the effective time period can be about 1 hour, 2 hour, about 4 hours, about 6 hours, about 8 hours, about 10 hours, about 12 hours, about 24 hours, or another time period determined to be effective by one of skill in the art. For example, the harmful time period can be about 12 hours, about 24 hours, about 48 hours, about 72 hours, about 144 hours, or another time period determined to be harmful by one of skill in the art.

In some embodiments, the therapeutically effective amount of the compound, product and/or pharmaceutical composition is selected to produce a blood concentration greater than the $IC_{50}$ of cells of the tumor and less than the $IC_{50}$ of normal cells. In some embodiments, the therapeutically effective amount is selected to produce a blood concentration sufficiently high to kill cells of the tumor and less than the $IC_{50}$ of normal cells.

In some embodiments, the compound, product and/or pharmaceutical composition is administered orally in a dosage form, for example, a tablet, pill, capsule (hard or soft), caplet, powder, granule, suspension, solution, gel, cachet, troche, lozenge, syrup, elixir, emulsion, oil-in-water emulsion, water-in-oil emulsion, and/or a draught.

The invention also provides kits and/or for of identifying or otherwise refining, e.g., stratifying, a patient population suitable for therapeutic administration of a compound of the disclosure by detecting the level of expression of one or more biomarkers associated with cancer stemness. A biomarker is deemed to be associated with cancer stemness when its expression is elevated in patient or sample from a patient suffering from a cancer known to have cancer stem cells and/or known to have aberrant Stat3 pathway activities as compared a baseline, control or normal level of expression of the same marker, e.g., the level in a patient that is not suffering from a cancer known to have cancer stem cells and/or known to have aberrant Stat3 pathway activities.

In some embodiments, the biomarker associated with cancer stemness is NANOG. In some embodiments, the biomarker associated with cancer stemness is STK33. In some embodiments, a combination of biomarkers associated with cancer stemness is used, where the combination is NANOG and STK33.

In the methods and/or kits of the disclosure, the level of expression of one or more cancer stemness markers is detected in a patient or a sample from a patient, and where the patient or sample has an elevated level of one or more cancer stemness markers as compared to a control level of expression, the patient is then administered a therapeutically effective amount of a compound of the disclosure.

In some embodiments of these methods, the method is an in vivo method. In some embodiments of these methods, the method is an in situ method. In some embodiments of these methods, the method is an ex vivo method. In some embodiments of these methods, the method is an in vitro method.

The disclosure also provides methods of treating a cancer in a human subject by administering to a subject in need thereof a therapeutically effective amount of a compound having the structure:

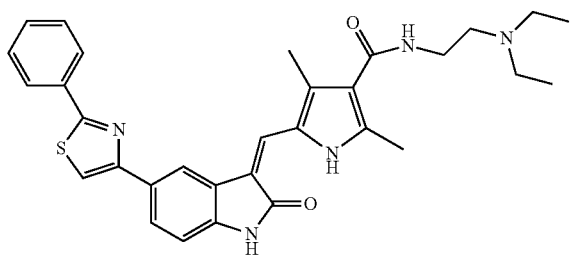 [SMILES: CCN(CC)CCNC(=O)c1c(C)[nH]c(/C=C2\C(=O)Nc3ccc(-c4csc(-c5ccccc5)n4)cc32)c1C]

or a pharmaceutically acceptable salt, solvate, hydrate, or prodrug thereof, wherein the compound is administered to the subject at a total daily dose of about 300 mg.

In some embodiments, the compound is administered to the subject in a single daily dose.

In some embodiments, the cancer is selected from the group consisting of colorectal cancer, colon cancer, rectal cancer, pancreatic cancer, pancreatic neuroendocrine tumor (PNET), gastroesophageal junction (GEJ) adenocarcinoma, gastric cancer, GEJ/gastric cancer, head and neck cancer, hepatocellular carcinoma (HCC), renal cell cancer (RCC), ovarian cancer, lung cancer, non-small cell lung cancer (NSCLC), small cell lung cancer (SCLC), breast cancer, prostate cancer, castration-resistant prostate cancer (CRPC), appendiceal cancer, melanoma, sarcoma, bladder cancer, gastrointestinal stromal tumors (GIST), and thyroid cancer.

In some embodiments, the cancer is colorectal cancer. In some embodiments, the cancer is refractory. In some embodiments, the cancer is recurrent. In some embodiments, the cancer is metastatic.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without parting from the spirit and scope of the invention. All references cited herein are incorporated by reference as if each had been individually incorporated.

The anti-cancer stem cell activity of a composition can be determined in vitro or in vivo. For example, antitumor activity of a composition can be determined in vitro by administering the compound and measuring the self-renewal and survival of cancer stem cells, For example, the antitumor activity of a compound can be assessed in vitro by comparing the behavior of tumor cells to which the compound has been administered with the behavior of tumor cells to which the compound has not been administered (a control). For example, antitumor activity of a composition can be determined in vivo by measuring, in an animal to which the compound has been administered, the change in volume of a tumor, by applying a metastatic model, and/or by applying an orthotopic model. For example, the antitumor activity of a compound can be assessed in vivo by comparing an animal to which the compound has been administered to an animal to which the compound has not been administered (a control).

The tolerability of a composition can be determined in vitro or in vivo. For example, tolerability of a composition can be determined in vitro by administering the compound and measuring the division rate of normal cells, by measuring the nutrient uptake of normal cells, by measuring indicators of metabolic rate of normal cells other than nutrient uptake, by measuring the growth of normal cells, and/or by measuring another indicator of the vitality of normal cells. For example, the tolerability of a compound can be assessed in vitro by comparing the behavior of normal cells to which the compound has been administered with the behavior of normal cells to which the compound has not been administered (a control). For example, tolerability of a composition can be determined in vivo by measuring, in an animal to which the compound has been administered, body weight or food intake or making clinical observations, such as hair retention or loss, activity, and/or responsiveness to stimuli. For example, the tolerability of a compound can be assessed in vivo by comparing an animal to which the compound has been administered to an animal to which the compound has not been administered (a control).

A compound, product and/or pharmaceutical composition can be assigned an effectivity rating and/or a toxicity rating. For example, the effectivity rating can be proportional to antitumor activity or can be a monotonically increasing function with respect to antitumor activity. For example, the toxicity rating can be inversely proportional to tolerability or can be a monotonically decreasing function with respect to tolerability. A naphthofuran compound has been reported to lack in vivo antitumor activity. See, M. M. Rao and D. G. I. Kingston, J. Natural Products, 45(5) (1982) 600-604. Furthermore, the compound has been reported to be equally toxic to cancer cells and normal cells. That is, the compound was reported as killing both cancer cells and normal cells equally, concluding the compound has no potential for cancer treatment. See, K. Hirai K. et al., Cancer Detection and Prevention, 23(6) (1999) 539-550; Takano A. et al., Anticancer Research 29:455-464, 2009.

However, experimental studies reported herein indicate that when the compound is administered as particles having an appropriate particle size distribution to achieve a certain pharmacokinetic exposure as described in this publication, the compound does have selective antitumor activity.

For the purposes of the present invention, "bioavailability" of a drug is defined as the relative amount of drug from an administered dosage form which enters the systemic circulation and the rate at which the drug appears in the blood stream. Bioavailability is governed by at least three factors: (i) absorption which controls bioavailability, followed by (ii) its tissue re-distribution and (iii) elimination (metabolic degradation plus renal and other mechanisms).

"Absolute bioavailability" is estimated by taking into consideration tissue re-distribution and biotransformation (i.e., elimination) which can be estimated in turn via intravenous administration of the drug. Unless otherwise indicated, "HPLC" refers to high performance liquid chromatography; "pharmaceutically acceptable" refers to physiologically tolerable materials, which do not typically produce an allergic or other untoward reaction, such as gastric upset, dizziness and the like, when administered to a mammal; "mammal" refers to a class of higher vertebrates including man and all other animals that nourish their young with milk secreted by mammary glands and have the skin usually more or less covered with hair; and "treating" is intended to encompass relieving, alleviating, or eliminating at least one symptom of a disease(s) in a mammal.

The term "treatment", as used herein, is intended to encompass administration of compounds according to the invention prophylactically to prevent or suppress an undesired condition, and therapeutically to eliminate or reduce the extent or symptoms of the condition. Treatment also includes preventing the relapse of an undesired condition, delaying the progression of an undesired condition, and preventing or delaying the onset of an undesired condition. Treatment according to the invention is given to a human or other mammal having a disease or condition creating a need of such treatment. Treatment also includes application of the compound to cells or organs in vitro. Treatment may be by systemic or local administration.

An effective amount is the amount of active ingredient administered in a single dose or multiple doses necessary to achieve the desired pharmacological effect. A skilled practitioner can determine an effective dose for an individual patient or to treat an individual condition by routine experimentation and titration well known to the skilled clinician. However, unexpected clinical responses from a patient population to a pharmaceutical formulation or composition may dictate unforeseen changes or adjustment to an aspect of the treatment such as the dosage, intervals in between drug administrations, and/or ways of drug administration. The actual dose and schedule may vary depending on whether the compositions are administered in combination with other drugs, or depending on inter-individual differences in pharmacokinetics, drug disposition, and metabolism. Similarly, amounts may vary for in vitro applications. Where disclosed herein, dose ranges, unless stated otherwise, do not necessarily preclude use of a higher or lower dose of a component, as might be warranted in a particular application.

The descriptions of pharmaceutical compositions provided herein include pharmaceutical compositions which are suitable for administration to humans. It will be understood by the skilled artisan, based on this disclosure, that such compositions are generally suitable for administration to any mammal or other animal. Preparation of compositions suitable for administration to various animals is well understood, and the ordinarily skilled veterinary pharmacologist can design and perform such modifications with routine experimentation based on pharmaceutical compositions for administration to humans.

Compound Structure and Properties

The compound used herein has the following structure:

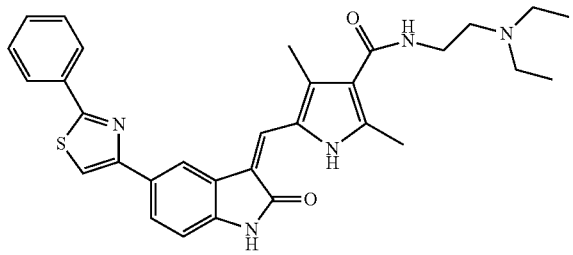 [SMILES: CCN(CC)CCNC(=O)c1c(C)[nH]c(/C=C2\C(=O)Nc3ccc(-c4csc(-c5ccccc5)n4)cc32)c1C]

Pharmaceutical Formulations

Certain excipients or enhancers were found to enhance the oral bioavailability of particles of a compound according to Formula I of a given particle size distribution in a pharmaceutical formulation. For example, the addition of the pharmaceutically compatible excipient GELUCIRE™ 44/14 (a polyethylene glycol glyceryl laurate produced by Gattefossé) can increase the bioavailability of Compound 1 having a median particle size of less than or equal to about 20 microns. Examples of other excipients than can be used to enhance or control oral bioavailability include surfactants, such as TWEEN 80™ or TWEEN 20™ (a polysorbate, i.e., a polyoxyethylene sorbitan monolaurate) or certain lipids, such as phosphatidylcholines, e.g., dimyristoylphosphatidylcholine (DMPC). Surfactants include compounds that are amphiphilic and contain both hydrophobic and hydrophilic groups. Other excipients can include, for example, a glycerol ester of a fatty acid, a glycerol ester of a saturated fatty acid, a glycerol ester of a saturated fatty acid having from 8 to 18 carbons, glyceryl laurate, polyethylene glycol, a polyoxyethylene sorbitan alkylate, cellulose or cellulose derivatives, such as microcrystalline cellulose and carboxymethyl cellulose (CMC), as well as lipids, such as sterols, e.g., cholesterol. Other excipients can include antioxidants, such as Vitamin E. Other excipients and additional components can be included in a pharmaceutical formulation according to the present invention, as will be appreciated by one of skill in the art. For example, other active agents, standard vehicles, carriers, liquid carriers, saline, aqueous solutions, diluents, surface active agents, dispersing agents, inert diluents, granulating and disintegrating agents, binding agents, lubricating agents, glidants, discharging agents, sweetening agents, flavoring agents, coloring agents, preservatives, physiologically degradable compositions such as gelatin, aqueous vehicles and solvents, oily vehicles and solvents, suspending agents, dispersing or wetting agents, suspending agents, emulsifying agents, demulcents, buffers, salts, thickening agents, gelatins, fillers, emulsifying agents, antioxidants, antibiotics, antifungal agents, stabilizing agents, water, glycols, oils, alcohols, crystallization retarding agents (e.g., to retard crystallization of a sugar), starches, sugars, sucrose, surface active agents, agents to increase the solubility of any other ingredient, such as a polyhydroxy alcohol, for example glycerol or sorbitol, pharmaceutically acceptable polymeric or hydrophobic materials, and other components can be included. The appropriate additional agent or agents to add will depend on the dosage form (e.g., injectable solution, capsule, or pill), as will be appreciated by one skilled in the art.

The compound according to Formula I of the present invention may be formulated into "pharmaceutical compositions". Embodiments according to the present invention include various dosage forms including a compound, which can be useful, for example, for treating a patient. For example, oral dosage forms can include a tablet, pill, capsule (hard or soft), caplet, powder, granule, suspension (e.g., in an aqueous or oily vehicle), solution (e.g., in an aqueous or oily vehicle), gel, cachet, troche, lozenge, syrup, elixir, emulsion, draught, oil-in-water emulsion, or a water-in-oil emulsion. Because of their ease in administration, tablets and capsules may represent a preferred oral dosage. Solid oral dosage forms may be sugar coated or enteric coated by standard techniques. For example, nasal and other mucosal spray formulations (e.g. inhalable forms) can include purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier, of an inhalant, or of an aerosol. Such formulations may be delivered by any suitable means or method, e.g., by nebulizer, atomizer, metered dose inhaler, or the like. For example, a pharmaceutical composition according to the present invention may be administered topically, for example, in the form of an ointment, cream, or suppository. For example, a pharmaceutical composition according to the present invention may be administered by injecting an injectant. Thus, a dosage form according to the present invention can have, for example, a solid, semi-solid, liquid, or gaseous form. Suitable dosage forms include but are not limited to oral, rectal, sub-lingual, mucosal, nasal, ophthalmic, subcutaneous, intramuscular, intravenous, parenteral, transdermal, spinal, intrathecal, intra-articular, intra-arterial, sub-arachinoid, bronchial, lymphatic, and intra-uterile administration, and other dosage forms for systemic delivery of active ingredients. An active ingredient, for example, a compound according to Formula I may be contained in a formulation that provides quick release, sustained release, delayed release, or any other release profile known to one skilled in the art after administration to a subject (patient). The mode of administration and dosage form selected for a given treatment is closely related to the therapeutic amounts of the compounds or compositions which are desirable and efficacious for the given treatment application as well as factors such as the mental state and physical condition of the subject (patient).

A pharmaceutical composition of the invention may be prepared, packaged, or sold in bulk, as a single unit dose, as a plurality of single unit doses, or in a multi-dose form. As used herein, a "unit dose" is a discrete amount of the pharmaceutical composition including a predetermined amount of the active ingredient. The amount of the active ingredient in each unit dose is generally equal to the total amount of the active ingredient that would be administered or a convenient fraction of a total dosage amount such as, for example, one-half or one-third of such a dosage. A formulation of a pharmaceutical composition of the invention suitable for oral administration may be in the form of a discrete solid dosage unit. Each solid dosage unit contains a predetermined amount of the active ingredient, for example a unit dose or fraction thereof. As used herein, an "oily" liquid is one which includes a carbon or silicon based liquid that is less polar than water. In such pharmaceutical dosage forms, the active agent preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof. The compositions of the present invention can be provided in unit dosage form, wherein each dosage unit, e.g., a teaspoon, tablet, capsule, solution, or suppository, contains a predetermined amount of the active drug or prodrug, alone or in appropriate combination with other pharmaceutically active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect.

Dosage forms of the present pharmaceutical composition can be prepared by techniques known in the art and contain a therapeutically effective amount of an active compound or ingredient. Any technique known or hereafter developed may be used for the preparation of pharmaceutical compositions or formulations according to the invention. In general, preparation includes bringing the active ingredient into association with a carrier or one or more other additional components, and then, if necessary or desirable, shaping or packaging the product into a desired single- or multi-dose unit. Powdered and granular formulations according to the invention may be prepared using known methods or methods to be developed. Such formulations may be administered directly to a subject, or used, for example, to form tablets, fill capsules, or prepare an aqueous or oily suspension or solution by addition of an aqueous or oily vehicle thereto. A tablet may be made by compression or molding, or by wet granulation, optionally with one or more accessory ingredients. Compressed tablets may be prepared by compressing, in a suitable device, the active ingredient in a free-flowing form such as a powder or granular preparation. Molded tablets may be made by molding, in a suitable device, a mixture of the active ingredient, a pharmaceutically acceptable carrier, and at least sufficient liquid to moisten the mixture. Tablets may be non-coated, or they may be coated using methods known in the art or methods to be developed. Coated tablets may be formulated for delayed disintegration in the gastrointestinal tract of a subject, for example, by use of an enteric coating, thereby providing sustained release and absorption of the active ingredient. Tablets may further include ingredients to provide a pharmaceutically elegant and palatable preparation. Hard capsules including the active ingredient may be made using a physiologically degradable composition, such as gelatin. Such hard capsules include the active ingredient. Soft gelatin capsules including the active ingredient may be made using a physiologically degradable composition, such as gelatin. Such soft capsules include the active ingredient, which may be mixed with water or an oil medium. Liquid formulations of a pharmaceutical composition of the invention that are suitable for administration may be prepared, packaged, and sold either in liquid form or in the form of a dry product intended for reconstitution with water or another suitable vehicle prior to use. Liquid suspensions, in which the active ingredient is dispersed in an aqueous or oily vehicle, and liquid solutions, in which the active ingredient is dissolved in an aqueous or oily vehicle, may be prepared using conventional methods or methods to be developed. Liquid suspension of the active ingredient may be in an aqueous or oily vehicle. Liquid solutions of the active ingredient may be in an aqueous or oily vehicle. To prepare such pharmaceutical dosage forms, an active ingredient, e.g., a naphthofuran, can be intimately admixed with a pharmaceutical carrier according to conventional pharmaceutical compounding techniques. The carrier may take a wide variety of forms depending on the form of preparation desired for administration. In preparing the compositions in oral dosage form, any of the usual pharmaceutical media may be employed.

In some embodiments according to the present invention, an item of manufacture includes a container containing a therapeutically effective amount of a pharmaceutical composition including a compound according to Formula I. The container can include a pharmaceutically acceptable excipient. The container can include printed labeling instructions. For example, the printed labeling can indicate the dosage and frequency with which the pharmaceutical composition should be administered, and whether the composition should be administered with food or within a defined period of time before or after ingestion of food. The composition can be contained in any suitable container capable of holding and dispensing the dosage form that will not significantly interact with the composition. The labeling instructions can be consistent with the methods of treatment described herein. The labeling can be associated with the container by a means that maintains a physical proximity of the two. By way of non-limiting example, the container and the labeling may both be contained in a packaging material such as a box or plastic shrink wrap or may be associated with the instructions being bonded to the container such as with glue that does not obscure the labeling instructions or other bonding or holding means.

Methods for Treatment of Cancer

A method according to the present invention for treating, delaying the progression of, preventing a relapse of, alleviating a symptom of, or otherwise ameliorating a human, mammal, or animal subject afflicted with a neoplasm includes administering a therapeutically effective amount of a pharmaceutical composition including particles of a predetermined size distribution, for example, a compound according to the disclosure, a pure compound, a pure product and/or a pure pharmaceutical composition, so that the volume growth of the neoplasm is slowed, the volume growth of the neoplasm is stopped, the neoplasm decreases in volume, and/or a cancerous neoplasm is killed. A few examples of types of neoplasms that may be amenable to treatment by this method include solid tumors, malignant tumors, cancers, refractory cancers, recurrent cancers, metastatic tumors, neoplasms including cancer stem cells, neoplasms in which the STAT3 pathway is implicated, carcinomas, and sarcomas. A non-exhaustive list of cancers that may be amenable to treatment by administration of particles of a compound according to Formula I include the following: breast cancer, head and neck cancer, lung cancer, ovarian cancer, pancreatic cancer, colorectal carcinoma, prostate cancer, melanoma, sarcoma, liver cancer, brain tumor, leukemia, multiple myeloma, gastric cancer, and lymphoma. The STAT3 pathway may be implicated in these cancers. A non-exhaustive list of cancers that may be amenable to treatment by administration of particles of, for example, a compound according to Formula I include the following: colorectal cancer, breast cancer, ovarian cancer, lung cancer, melanoma and medulloblastoma. The CSC pathway may be implicated in these cancers. A non-exhaustive list of other cancers that may be amenable to treatment by administration of particles of, for example, a compound according to the disclosure include the following: lung cancer, cervical cancer, renal cell carcinoma, hepatocellular carcinoma, esophageal cancer, glioma, bladder cancer, colorectal cancer, breast cancer, prostate cancer, pancreatic cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer.

In embodiments of the invention, a therapeutically effective amount of the Compound of the Invention or a pharmaceutically acceptable salt, solvate, hydrate, or prodrug thereof is administered to a patient or subject diagnosed of a cancer, wherein the cancer is gastroesophageal junction cancer, an esophageal cancer, or gastroesophageal adenocarcinoma. Optionally, an antimitotic agent such as paclitaxel is administered as a second/combinatorial agent for co-therapy.

Cancer Stem Cells

In recent years, a new model of tumorigenesis has gained wide acceptance, where it is hypothesized that only a small fraction of the entire tumor mass are responsible for the tumorigenic activities within the tumor, whereas the old or clonal genetic model posits that all the mutated tumor cells contribute equally to such tumorigenic activities. This small fraction of tumorigenic cells, according to the new model, are transformed cells with stem-cell-like qualities and are called "cancer stem cells" (CSCs). Bonnet and Dick first demonstrated, in vivo, the presence of CSCs in acute myeloid leukemia (AML) during the 1990s. Their data showed that only a small subpopulation of human AML cells had the ability to transfer AML when transplanted into immunodeficient mice while other AML cells were incapable of inducing leukemia. Later, these CSCs were shown to have the same cellular markers, $CD34^+/CD38^-$, as primitive hematopoietic stem cells. (Bonnet, D., *Normal and leukaemic stem cells*. Br J Haematol, 2005. 130(4): p. 469-79). Since then, researchers have found CSCs conclusively in various types of tumors including those of the brain, breast, skin, prostate, colorectal cancer, and so on.

The CSC model of tumorigenesis would explain why tens or hundreds of thousands of tumor cells need to be injected into an experimental animal in order to establish a tumor transplant. In human AML, the frequency of these cells is less than 1 in 10,000. (Bonnet, D. and J. E. Dick, *Human acute myeloid leukemia is organized as a hierarchy that originates from a primitive hematopoietic cell*. Nat Med, 1997. 3(7): p. 730-7). Even though rare within a given tumor cell population, there is mounting evidence that such cells exist in almost all tumor types. However, as cancer cell lines are selected from a sub-population of cancer cells that are specifically adapted to grow in tissue culture, the biological and functional properties of cancer cell lines can undergo dramatic changes. Therefore, not all cancer cell lines contain CSCs.

Cancer stem cells share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types, which would explain histological evidence that not only many tumors contain multiple cell types native to the host organ, but also that heterogeneity is commonly retained in tumor metastases. CSCs have been demonstrated to be fundamentally responsible for tumorigenesis, cancer metastasis, and cancer reoccurrence. CSCs are also called tumor initiating cells, cancer stem-like cells, stem-like cancer cells, highly tumorigenic cells, tumor stem cells, solid tumor stem cells, or super malignant cells.

The existence of cancer stem cells has fundamental implications for future cancer treatments and therapies. These implications are manifested in disease identification, selective drug targeting, prevention of cancer metastasis and recurrence, and development of new strategies in fighting cancer.

The efficacy of current cancer treatments is, in the initial stages of testing, often measured by the size of the tumor shrinkage, i.e., the amount of tumor mass that is killed off. As CSCs would form a very small proportion of the tumor and have markedly different biologic characteristics than their more differentiated progenies, the measurement of tumor mass may not necessarily select for drugs that act specifically on the stem cells. In fact, cancer stem cells appear to be resistant to radiotherapy (XRT) and also refractory to chemotherapeutic and targeted drugs. (Hambardzumyan, D., M. Squatrito, and E. C. Holland, Radiation resistance and stem-like cells in brain tumors. Cancer Cell, 2006. 10(6): p. 454-6; Baumann, M., M. Krause, and R. Hill, Exploring the role of cancer stem cells in radioresistance. Nat Rev Cancer, 2008. 8(7): p. 545-54; Ailles, L. E. and I. L. Weissman, Cancer stem cells in solid tumors. Curr Opin Biotechnol, 2007. 18(5): p. 460-6). Normal somatic stem cells are naturally resistant to chemotherapeutic agents—they have various pumps (such as MDR) that pump out drugs, and DNA repair proteins. Further, they also have a slow rate of cell turnover while chemotherapeutic agents target rapidly replicating cells. Cancer stem cells, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to generate new highly tumorigenic cancer stem cells. The population of cancer stem cells that gave rise to the differentiated and differentiating cells, on the other hand, could remain untouched and cause a relapse of the disease. A further danger for conventional anti-cancer therapy is the possibility that chemotherapeutic treatment leaves only chemotherapy-resistant cancer stem cells, and the ensuing recurrent tumor will likely also be resistant to chemotherapy.

Since the surviving cancer stem cells can repopulate the tumor and cause relapse, it is imperative that anti-cancer therapies include strategies against CSCs (see FIG. 18 of WO 2011/116398 and WO 2011/116399). This is akin to eliminating the roots in order to prevent dandelions from regrowth even if the weed's ground level mass has been cut. (Jones, R. J., W. H. Matsui, and B. D. Smith, *Cancer stem cells: are we missing the target?* J Natl Cancer Inst, 2004. 96(8): p. 583-5). By selectively targeting cancer stem cells, it becomes possible to treat patients with aggressive, non-resectable tumors and refractory or recurrent cancers, as well as preventing the tumor metastasis and recurrence. Development of specific therapies targeting cancer stem cells may improve survival and the quality of life of cancer patients, especially for sufferers of metastatic cancers. The key to unlocking this untapped potential is the identification and validation of pathways that are selectively important for cancer stem cell self-renewal and survival. Unfortunately, though multiple pathways underlying tumorigenesis in cancer or self-renewal in embryonic and adult stem cells have been elucidated in the past, very few pathways have been identified and validated for cancer stem cell self-renewal and survival.

There has also been a lot of research into the identification and isolation of cancer stem cells. Methods used mainly exploit the ability of CSCs to efflux drugs, or are based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1) (Ho, M. M., et al., Side population in human lung cancer cell lines and tumors is enriched with stem-like cancer cells. Cancer Res, 2007. 67(10): p. 4827-33; Wang, J., et al., Identification of cancer stem cell-like side population cells in human nasopharyngeal carcinoma cell line. Cancer Res, 2007. 67(8): p. 3716-24; Haraguchi, N., et al., Characterization of a side population of cancer cells from human gastrointestinal system. Stem Cells, 2006. 24(3): p. 506-13; Doyle, L. A. and D. D. Ross, Multidrug resistance mediated by the breast cancer resistance protein BCRP (ABCG2). Oncogene, 2003. 22(47): p. 7340-58; Alvi, A. J., et al., Functional and molecular characterisation of mammary side population cells. Breast Cancer Res, 2003. 5(1): p. R1-8), and other ATP binding cassette (ABC) superfamily members (Frank, N.Y., et al., ABCB5-mediated doxorubicin transport and chemoresistance in human malignant melanoma. Cancer Res, 2005. 65(10): p. 4320-33; Schatton, T., et al., Identification of cells initiating human melanomas. Nature, 2008. 451(7176): p. 345-9). Accordingly, the side population (SP) technique, originally used to enrich hematopoietic and leukemic stem cells, was also employed to identify and isolate CSCs. (Kondo, T., T. Setoguchi, and T. Taga, *Persistence of a small subpopulation of cancer stem-like cells in the C6 glioma cell line*. Proc Natl Acad Sci USA, 2004. 101(3): p. 781-6). This technique, first described by Goodell et al., takes advantage of differential ABC transporter-dependent efflux of fluorescent dyes such as Hoechst 33342 to define and isolate a cell population enriched in CSCs (Doyle, L. A. and D. D. Ross, *Multidrug resistance mediated by the breast cancer resistance protein BCRP (ABCG2)*. Oncogene, 2003. 22(47): p. 7340-58; Goodell, M. A., et al., *Isolation and functional properties of murine hematopoietic stem cells that are replicating in vivo*. J Exp Med, 1996. 183(4): p. 1797-806). Specifically, the SP is revealed by blocking drug efflux with verapamil, at which point the dyes can no longer be pumped out of the SP.

Researchers have also focused on finding specific markers that distinguish cancer stem cells from the bulk of the tumor. Most commonly expressed surface markers by the cancer stem cells include CD44, CD133, and CD166. (Collins, A. T., et al., Prospective identification of tumorigenic prostate cancer stem cells. Cancer Res, 2005. 65(23): p. 10946-51; Li, C., et al., Identification of pancreatic cancer stem cells. Cancer Res, 2007. 67(3): p. 1030-7; Ma, S., et al., Identification and characterization of tumorigenic liver cancer stem/progenitor cells. Gastroenterology, 2007. 132(7): p. 2542-56; Prince, M. E., et al., Identification of a subpopulation of cells with cancer stem cell properties in head and neck squamous cell carcinoma. Proc Natl Acad Sci USA, 2007. 104(3): p. 973-8; Ricci-Vitiani, L., et al., Identification and expansion of human colon-cancer-initiating cells. Nature, 2007. 445(7123): p. 111-5; Singh, S. K., et al., Identification of a cancer stem cell in human brain tumors. Cancer Res, 2003. 63(18): p. 5821-8; Dalerba, P., et al., Phenotypic characterization of human colorectal cancer stem cells. Proc Natl Acad Sci USA, 2007. 104(24): p. 10158-63). Sorting tumor cells based primarily upon the differential expression of these surface marker(s) have accounted for the majority of the highly tumorigenic CSCs described to date. Therefore, these surface markers are well validated for identification and isolation of cancer stem cells from the cancer cell lines and from the bulk of tumor tissues.

Recent studies have uncovered the presence of cancer stem cells (CSCs) with an exclusive ability to regenerate tumors. These CSCs exist in almost all tumor types and are functionally linked with continued malignant growth, cancer metastasis, recurrence, and cancer drug resistance. CSCs and their more differentiated progenies appear to have markedly different biologic characteristics. Conventional cancer drug screenings depend on measurement of the amount of tumor mass, therefore, they may not necessarily select for drugs that act specifically on the CSCs. In fact, CSCs have been demonstrated to resistant to standard chemotherapies and radiotherapy, and to becoming enriched after standard anti-cancer treatments, which result in cancer refractory and recurrence. Methods of isolating these cells include but not limited to identification by their ability of efflux Hoechst 33342, identification by the surface markers these cells express, such as CD133, CD44, CD166, and others, and enrichment by their tumorigenic property. The mounting evidence linking cancer stem cells to tumorigenesis unravel enormous therapeutic opportunity of targeting cancer stem cells.

The data provided herein, combined with recent breakthroughs in CSC research, allows the present invention to provide an array of methods directed at inhibiting CSCs, methods directed at inhibiting both CSCs and heterogeneous cancer cells, and methods of treating cancers that have CSCs in specific or cancers in general. The present invention also provides related methods (e.g., manufacturing and drug candidate screening), materials, compositions and kits. The method can prevent the CSCs from self-renewal, such that it is no longer able to replenish its numbers by dividing into tumorigenic CSC cells. Or, the method can induce cell death in CSCs, or in both CSCs and heterogeneous cancer cells.

This method can be used to treat a subject's cancer. Cancers that are good candidates for such treatment include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas. In some embodiments, the method is used to treat liver cancers, head and neck cancers, pancreatic cancers, and/or gastric cancers. In some embodiments, the method is used to treat multiple myeloma, brain tumors, and sarcomas.

Further, as CSCs have been demonstrated to be fundamentally responsible for tumorigenesis, cancer metastasis and cancer reoccurrence, any methods of the invention directed to inhibiting CSCs, or both CSCs and heterogeneous cancer cells, can be practiced to treat cancer that is metastatic, refractory to a chemotherapy or radiotherapy, or has relapsed in the subject after an initial treatment.

In some embodiments, the cancer stem cell inhibitor according to the present invention is a compound having the following structure:

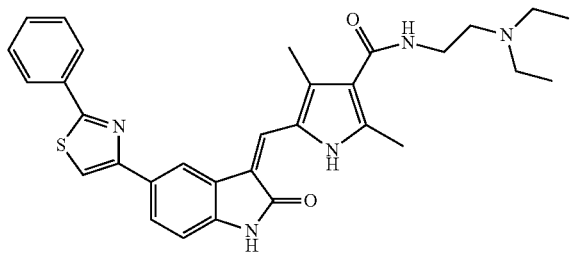 [SMILES: CCN(CC)CCNC(=O)c1c(C)[nH]c(/C=C2\C(=O)Nc3ccc(-c4csc(-c5ccccc5)n4)cc32)c1C]

an enantiomer, diastereomer, tautomer, and a salt or solvate thereof (also referred to herein as the "Compound of the Invention").

The present invention provides a method of identifying a drug candidate capable of inhibiting a cancer stem cell. In some embodiments, the drug candidate is capable of inducing cell death in CSC or at least inhibiting its self-renewal. In a further embodiment, the drug candidate is capable of inducing cell death in CSC or at least inhibiting its self-renewal, and inducing cell death in heterogeneous cancer cells. Various phases in the pathway can be targeted for screening the drug candidate.

Accordingly, in another aspect, the Compound of the Invention can be used to formulate a pharmaceutical composition to treat or prevent disorders or conditions. Some of the disorders include but are not limited to: autoimmune diseases, inflammatory diseases, inflammatory bowel diseases, arthritis, autoimmune demyelination disorder, Alzheimer's disease, stroke, ischemia reperfusion injury and multiple sclerosis. Some of the disorders are cancers and include but are not limited to: various types of breast cancers, head and neck cancers, lung cancers, ovarian cancers, pancreatic cancers, colorectal carcinoma, prostate cancers, renal cell carcinoma, melanoma, hepatocellular carcinomas, cervical cancers, sarcomas, brain tumors, gastric cancers, multiple myeloma, leukemia, and lymphomas.

Accordingly, in an aspect, the present invention provides a method of inhibiting cancer stem cells where an effective amount of the Compound of the Invention is administered to the cells. Cancers known to have CSCs are good candidates for such treatments, and include but are not limited to: various types of breast cancers, head and neck cancers, lung cancers, ovarian cancers, pancreatic cancers, colorectal adenocarcinoma, prostate cancers, liver cancers, melanoma, multiple myeloma, brain tumors, sarcomas, medulloblastoma, and leukemia.

Further, as CSCs have been demonstrated to be fundamentally responsible for tumorigenesis, cancer metastasis and cancer reoccurrence, any methods of the invention directed to inhibiting CSCs can be practiced to treat cancer that is metastatic, refractory to a chemotherapy or radiotherapy, or has relapsed in the subject after an initial treatment.

In some embodiments of the method, the cancer being treated is selected from the following group: liver cancer, colon cancer, head and neck cancer, pancreatic cancer, gastric cancer, renal cancer, sarcoma, multiple myeloma, metastatic breast cancer, metastatic prostate cancer, leukemia, lymphoma, pancreatic esophageal cancer, brain tumor, glioma, bladder cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer. The cancer may implicate malfunction of the STAT3, Nanog and/or β-catenin pathway.

In an aspect, the present invention provides a method of treating cancer in a subject, where a therapeutically effective amount of a pharmaceutical composition including the Compound of the Invention is administered to the subject. The cancer may be metastatic, refractory or recurrent. The subject may be a mammal, e.g., a human being.

Treatment by administration of a compound according to the disclosure to a subject (patient) suffering from a neoplasm may be indicated for the following conditions. The neoplasm may be refractory to treatment by chemotherapy, radiotherapy, or hormone therapy. The neoplasm may not be amenable to surgical resection. The neoplasm may have relapsed in the subject (patient). Cancer stem cells have been implicated in the relapse of neoplasms; killing the cancer stem cells or inhibiting their self-renewal by a method according to the present invention may prevent the neoplasm from regenerating itself. Treatment by administration of particles of naphthofuran may slow or stop the volume growth of a neoplasm or decrease the volume of a neoplasm by, for example, inducing the death of, inhibiting the growth and/or division of, and/or selectively killing neoplastic cells. For example, a treatment according to the present invention may induce cell death of a cell of the neoplasm. For example, the treatment may act to inhibit the STAT3, Nanog and/or β-catenin pathway of a neoplastic cell.

Treatment by administration of particles of, for example, a Compound of the Invention to a subject (patient) suffering from a neoplasm may be used to prevent relapse of a neoplasm and/or as an adjuvant therapy to surgical resection.

A pharmaceutical composition including particles of, for example, a Compound of the Invention may be administered orally, as this is a convenient form of treatment. For example, the pharmaceutical composition may be administered orally no more than four times per day. Alternatively, the pharmaceutical composition can be administered intravenously or intraperitoneally.

Patient Screening Using Putative Biomarker

The invention provides kits and/or for of identifying or otherwise refining, e.g., stratifying, a patient population suitable for therapeutic administration of a compound of the disclosure by detecting the level of expression of one or more biomarkers associated with cancer stemness. In the methods and/or kits of the disclosure, the level of expression of one or more cancer stemness markers is detected in a patient or a sample from a patient, and where the patient or sample has an elevated level of one or more cancer stemness markers as compared to a control level of expression, the patient is then administered a therapeutically effective amount of a compound of the disclosure. In some embodiments of these methods, the method is an in vivo method. In some embodiments of these methods, the method is an in situ method. In some embodiments of these methods, the method is an ex vivo method. In some embodiments of these methods, the method is an in vitro method.

Understanding the clinical relevance of the stemness markers and identifying predictive biomarkers assists clinical development by selecting patients that will most likely to derive clinical benefit from treatment with the Compound of the Invention. In current studies, we studied stemness gene marker in biopsy tumor as well as archival tumor samples from patients. In the needle biopsy tumor samples collected before and after 28 days treatment of the Compound of the Invention from phase I patients, the Compound of the Invention is potent in reducing nuclear NANOG and STK33 in patient with positive NANOG and STK33 staining. Archival tissue from patients receiving the Compound of the Invention was analyzed via immunohistochemistry to determine whether response to the drug was correlated with either NANOG or STK33. Patients with high levels of nuclear staining for STK33 were more likely to respond to treatment with the Compound of the Invention with improved (SD, MR, PR) as compared to those that did not show a response (PD). Furthermore, following treatment with Compound of the Invention, patients that had high levels of nuclear STK33 also showed improved Median progression free survival (PFS, $P<0.0273$) and overall survival ($P<0.0097$). The nuclear NANOG expression demonstrated a similar trend. Importantly, 90.9% of the tumors with STK33 nuclear staining were also positive for nuclear NANOG staining and there was a significant correlation between nuclear STK33 and nuclear NANOG ($P<0.0022$).

Thus, cancer stemness markers NANOG and STK33 are successful biomarkers for predicting responsiveness of patients to treatment with a Compound of the Invention thus targeting the CSC population making this a promising new developments in cancer chemotherapy In various embodiments of the above treatment methods, the cancer may be one of the following: esophageal cancer, gastroesophageal junction cancer, gastroesophageal adenocarcinoma, colorectal adenocarcinoma, breast cancer, ovarian cancer, head and neck cancer, melanoma, angiosarcoma, gastric adenocarcinoma, lung, prostate and adrenocorticoid. The cancer may be refractory, recurrent or metastatic.

Drug Regimen, Dosage and Interval

In a method according to the present invention, the therapeutically effective amount of the pharmaceutical composition including particles, polymorphs and/or purified forms of a Compound of the Invention can be a total daily dose in the range from about 20 mg to about 2000 mg, from about 100 mg to about 1500 mg, from about 160 mg to about 1400 mg, or from about 180 mg to about 1200 mg. In some embodiments, the therapeutically effective amount of the pharmaceutical composition including particles, polymorphs and/or purified forms of a Compound of the Invention is a total daily dose in the range of from about 200 mg to about 1500 mg, or from about 360 mg to 1200 mg. In some embodiments, the therapeutically effective amount of the pharmaceutical composition including particles, polymorphs and/or purified forms of a Compound of the Invention is a total daily dose in the range of from about 400 mg to about 1000 mg. In some embodiments, the therapeutically effective amount of the pharmaceutical composition including particles, polymorphs and/or purified forms of a Compound of the Invention is a total daily dose of about 1000 mg.

Intervals between each dose can vary or stay constant, depending on factors such as pharmacokinetics of the composition, drug metabolism with or without intake of fluid or food, tolerability and other drug adherence factors (e.g., convenience). A preferred interval maintains an effective level of the pharmaceutical composition in the body while causing minimal adverse side effects. In some embodiments, the interval between each dose ranges from about 4 hours to about 24 hours. In some embodiments, the interval between each dose ranges from about 8 hours to about 14 hours. In some embodiments, the interval between each dose ranges from about 10 hours to about 13 hours, or, is about 12 hours. Accordingly in those embodiments, the compound is administered to the subject about twice daily, for example, on average over the duration of a regimen.

A Compound of the Invention or a pharmaceutical composition thereof can be administered through any one of or through a combination of routes, for example, orally, intravenously, or intraperitoneally. For example, in some embodiments, a Compound of the Invention can be administered orally. In some embodiments, a Compound of the Invention can be administered orally in a formulation that includes Gelucire and Tween 80, or a formulation that includes Gelucire (lauroyl polyoxylglycerides), Labrafil (linoleoyl polyoxylglycerides), and a surfactant such as sodium lauryl sulfate (SLS) or sodium dodecyl sulfate (SDS).

If the condition of the subject (patient) so requires, doses of the pharmaceutical composition may be administered as a continuous or pulsatile infusion. The duration of a treatment may be decades, years, months, weeks, or days, as long as the benefits persist. The foregoing ranges are provided only as guidelines and are subject to optimization.

In a method according to the invention, cells of the neoplasm are selectively killed by administering the pharmaceutical composition, so that the blood molar concentration of the compound is at least an effective concentration and less than a harmful concentration for a first continuous time period that is at least as long as an effective time period and shorter than a harmful time period. The blood molar concentration can be less than the effective concentration after the first continuous time period. The effective concentration can be a concentration sufficiently high, so that neoplastic cells, e.g., cancer cells, are killed. The effective time period can be sufficiently long, so that neoplastic cells, e.g., cancer cells, are killed. The harmful concentration can be a concentration at which normal cells are damaged or killed. The harmful time period can be a time period sufficiently long for normal cells to be damaged or killed.

One of skill in the art can administer the pharmaceutical composition by selecting dosage amount and frequency so as to achieve a herein described "selective pharmacokinetic profile" (SPP) deemed necessary for selective killing neoplastic cells, such as cancer cells, and sparing normal cells. Such consideration of the SPP can also guide the design of the pharmaceutical composition, for example, the particle size distribution and distribution of shapes of the particles.

In a method according to the invention, the pharmaceutical composition is administered orally in a dosage form such as a tablet, pill, capsule (hard or soft), caplet, powder, granule, suspension, solution, gel, cachet, troche, lozenge, syrup, elixir, emulsion, oil-in-water emulsion, water-in-oil emulsion, or draught.

EXAMPLE 1

Dose Escalation Study of the Compound of the Invention in Adult Patients with Advanced Solid Tumors The studies described herein were designed to determine safety, tolerability, Recommended Phase II Dose (RP2D), pharmacokinetics and preliminary anti-tumor activity of the Compound of the Invention, an orally-administered first-in-class multi-kinase inhibitor with potent activity against cancer stem cells (CSCs). Preclinically, potent anti-CSC and broad-spectrum anti-tumor and anti-metastatic activity was seen in vitro and in vivo.

In this study, the Compound of the Invention was given orally, continuously, in 28-day cycles until disease progression, unacceptable toxicity, or other discontinuation criteria were met.

Escalating doses from 10 mg to 450 mg once daily were administered to 26 patients. Maximum tolerated dose (MTD) was not reached. The Compound of the Invention was well tolerated, with mild GI adverse events, including grade 1, 2 diarrhea, abdominal cramping, nausea, anorexia. Grade 3 diarrhea was observed in 2 subjects at 450 mg once daily. The Compound of the Invention exhibited favorable pharmacokinetics with dose-dependent increases in plasma concentration up to 300 mg once daily. Inhibition of cancer stem cell markers was observed in biopsied tumor tissues. Of 20 evaluable patients, 11 (55%) had stable disease (SD) with a median time to progression of 16 weeks. Of those patients with SD, tumor regression and/or prolonged stable disease (≥16 weeks) were observed in 10 (50% of all enrolled patients), as shown below in Table 1:

TABLE 1

| Diagnosis | Number of Patients Evaluable | Number of Patients with minor regression or SD ≥16 wks. |
|---|---|---|
| Colorectal Cancer | 5 | 3 |
| Head & Neck Cancer | 2 | 2 |
| Hepatocellular Carcinoma | 2 | 1 |
| Renal Cell Carcinoma | 1 | 1 |
| Gastric/GEJ Adenocarcinoma | 1 | 1 |
| Pancreatic Neuroendocrine | 1 | 1 |
| Non-Small Cell Lung Cancer | 1 | 1 |

The Compound of the Invention, a first-in-class cancer stemness kinase inhibitor, administered orally once daily was well tolerated, with once daily RP2D determined to be 300 mg. Pharmacokinetic exposure well above the predicted therapeutic level was achieved, and inhibition of cancer stem cell markers was observed in biopsied tumor tissue. Encouraging signs of anti-tumor activity have been observed in pretreated patients with advanced cancer.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method of therapeutically treating a cancer in a subject comprising administering to a subject in need thereof a therapeutically effective amount of a compound having the structure:

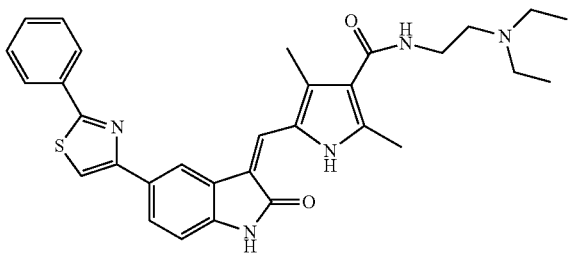 [SMILES: CCN(CC)CCNC(=O)c1c(C)[nH]c(/C=C2\C(=O)Nc3ccc(-c4csc(-c5ccccc5)n4)cc32)c1C]

or a pharmaceutically acceptable salt, solvate, hydrate, or prodrug thereof orally, continuously, in 28-day cycles.

2. The method of claim 1, wherein the compound is administered to the subject in a single daily dose.

3. The method of claim 1, wherein the cancer is selected from the group consisting of colorectal cancer, colon cancer, rectal cancer, pancreatic cancer, pancreatic neuroendocrine tumor (PNET), gastroesophageal junction (GEJ) adenocarcinoma, gastric cancer, GEJ/gastric cancer, head and neck cancer, hepatocellular carcinoma (HCC), renal cell cancer (RCC), ovarian cancer, lung cancer, non-small cell lung cancer (NSCLC), small cell lung cancer (SCLC), breast cancer, prostate cancer, castration-resistant prostate cancer (CRPC), appendiceal cancer, melanoma, sarcoma, bladder cancer, gastrointestinal stromal tumors (GIST), and thyroid cancer.

4. The method of claim 1, wherein the cancer is colorectal cancer.

5. The method of claim 1, wherein the cancer is refractory.

6. The method of claim 1, wherein the cancer is recurrent.

7. The method of claim 1, wherein the cancer is metastatic.

8. A method of therapeutically treating cancer in a comprising administering to a subject a therapeutically effective amount of a compound having the structure

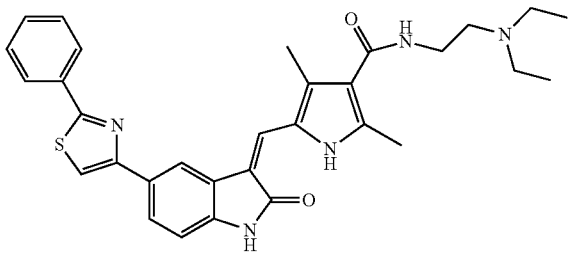 [SMILES: CCN(CC)CCNC(=O)c1c(C)[nH]c(/C=C2\C(=O)Nc3ccc(-c4csc(-c5ccccc5)n4)cc32)c1C]

or a pharmaceutically acceptable salt, solvate, hydrate, or prodrug thereof, wherein the subject has an elevated expression of one or more biomarkers each selected from NANOG or STK33.

9. The method of claim 8, wherein the cancer is selected from the group consisting of colorectal cancer, colon cancer, rectal cancer, pancreatic cancer, pancreatic neuroendocrine tumor (PNET), gastroesophageal junction (GEJ) adenocarcinoma, gastric cancer, GEJ/gastric cancer, head and neck cancer, hepatocellular carcinoma (HCC), renal cell cancer (RCC), ovarian cancer, lung cancer, non-small cell lung cancer (NSCLC), small cell lung cancer (SCLC), breast cancer, prostate cancer, castration-resistant prostate cancer (CRPC), appendiceal cancer, melanoma, sarcoma, bladder cancer, gastrointestinal stromal tumors (GIST), and thyroid cancer.

10. The method of claim 8, wherein the cancer is colorectal adenocarcinoma.

11. The method of claim 8, wherein the cancer is refractory.

12. The method of claim 8, wherein the cancer is recurrent.

13. The method of claim 8, wherein the cancer is metastatic.

14. The method of claim 8, wherein the expression is detected in cell nuclei in a sample from the subject.

15. The method of claim 8, wherein the expression is localized.

16. The method of claim 1, wherein the subject has an elevated expression of one or more cancer stemness biomarkers.

17. The method of claim 16, wherein the one or more cancer stemness biomarkers comprises nuclear NANOG and/or STK33.

18. The method of claim 8, wherein the cancer is pancreatic cancer.

19. The method of claim 8, wherein the cancer is bladder cancer.

20. The method of claim 8, wherein the cancer is head and neck cancer.

21. The method of claim 8, wherein the cancer is hepatocellular carcinoma (HCC).

22. The method of claim 8, wherein the cancer is ovarian cancer.

23. The method of claim 1, wherein the cancer is bile duct cancer.

24. The method of claim 1, wherein the cancer is hepatocellular carcinoma (HCC).

25. The method of claim 1, wherein the cancer is bladder cancer.

26. The method of claim 1, wherein the cancer is renal cell cancer (RCC).

27. The method of claim 1, wherein the cancer is ovarian cancer.

28. The method of claim 8, wherein the cancer is bile duct cancer.

* * * * *